US009717589B2

(12) United States Patent
Simonov et al.

(10) Patent No.: US 9,717,589 B2
(45) Date of Patent: *Aug. 1, 2017

(54) ADJUSTABLE ACCOMMODATING INTRAOCULAR LENS AND POSITIONING MEANS

(75) Inventors: Aleksey Nikolaevich Simonov, Delft (NL); Michiel Christiaan Rombach, Breda (NL)

(73) Assignee: Akkolens International B.V., Breda (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/738,127

(22) PCT Filed: Oct. 2, 2008

(86) PCT No.: PCT/NL2008/050628
§ 371 (c)(1),
(2), (4) Date: Jun. 29, 2010

(87) PCT Pub. No.: WO2009/051477
PCT Pub. Date: Apr. 23, 2009

(65) Prior Publication Data
US 2010/0280609 A1    Nov. 4, 2010

(30) Foreign Application Priority Data

Oct. 15, 2007  (EP) .................................... 07118512
Nov. 23, 2007  (EP) .................................... 07121454

(51) Int. Cl.
A61F 2/16    (2006.01)
(52) U.S. Cl.
CPC .......... *A61F 2/1632* (2013.01); *A61F 2/1648* (2013.01); *A61F 2002/1682* (2015.04)

(58) Field of Classification Search
CPC .... A61F 2/1624; A61F 2/1632; A61F 2/1648; A61F 2/1651; A61F 2002/1682
(Continued)

(56) References Cited

U.S. PATENT DOCUMENTS 4,664,666 A *  5/1987  Barrett ........................ 623/6.44
4,994,082 A    2/1991  Richards et al.
2007/0129799 A1  6/2007  Schedler

FOREIGN PATENT DOCUMENTS

EP    0094158 A1   11/1983
EP    1720489 A2   11/2006
(Continued)

OTHER PUBLICATIONS

Search Report and Written Opinion for International Patent Application No. PCT/NL2008/050628; May 29, 2009.

*Primary Examiner* — David H Willse
*Assistant Examiner* — Javier Blanco
(74) *Attorney, Agent, or Firm* — The Webb Law Firm

(57) ABSTRACT

An accommodating intraocular artificial lens with variable optical power, comprising two optical elements which are adapted to mutually shift in a direction perpendicular to the optical axis wherein the optical elements have such a shape that the optical elements exhibit, in combination, different optical powers at different relative positions. Flanges are adapted to position the anterior section of the haptics in the sulcus of the eye or, alternatively, the ciliary body is enclosed by a combination of anterior and posterior flanges. Also disclosed are methods to provide for an accommodating intraocular lens which is adjustable post-implant to ensure emmetropia of the eye.

15 Claims, 2 Drawing Sheets

(58) Field of Classification Search
USPC .............................................. 623/6.34, 6.37
See application file for complete search history.

(56) References Cited

FOREIGN PATENT DOCUMENTS

| | | | | |
|---|---|---|---|---|
| EP | 1890650 | A2 | 2/2008 | |
| NL | 1028496 | C2 | 9/2006 | |
| WO | 03017873 | A1 | 3/2003 | |
| WO | 03058287 | A2 | 7/2003 | |
| WO | 2005065600 | A1 | 7/2005 | |
| WO | 2005/084587 | * | 9/2005 | |
| WO | 2005104994 | A2 | 11/2005 | |
| WO | 2006/118452 | A1 | 11/2006 | |
| WO | WO 2006118452 A1 * | | 11/2006 | ............... A61F 2/16 |
| WO | 2007015640 | A1 | 2/2007 | |
| WO | 2007027091 | A2 | 3/2007 | |

\* cited by examiner

ADJUSTABLE ACCOMMODATING INTRAOCULAR LENS AND POSITIONING MEANS

PRIORITY CLAIM

This patent application is a U.S. National Phase of International Patent Application No. PCT/NL2008/050628, filed Oct. 2, 2008, which claims priority to co-pending European Patent Application No. 07118512.8, filed Oct. 15, 2007, and co-pending European Patent Application No. 07121454.8, filed Nov. 23, 2007, the disclosures of which are incorporated herein by reference in their entirety.

FIELD

The present disclosure relates to positioning in the eye and adjustment of an accommodating intraocular artificial lens, a lens with variable optical power, comprising two optical elements which are adapted to mutually move (by shift, rotation or combination thereof) in a direction perpendicular to the optical axis wherein the optical elements have such a shape that the optical elements exhibit, in combination, different optical powers at different relative positions.

BACKGROUND

For purposes of the present disclosure, the following abbreviations and definitions will be used.

"IOL" for intraocular lens, which is an artificial lens for the eye implanted by an eye surgeon, including, but not limited to, monofocal lenses, multifocal lenses, phakic and a-phakic lenses and accommodating intraocular lenses.

"MIOL" for monofocal intraocular lens, which is a traditional intraocular lens with one focus.

"AIOL" for accommodating intraocular lens, which is an artificial lens which changes diopter power to focus the eye, driven by the natural mechanism for focusing by the ciliary muscle.

"AAIOL" for adjustable accommodating intraocular lens, of which the basic power can be adjusted, generally to improve emmetropia of the eye during surgery or post-surgery.

"Ciliary body" refers to numerous muscle filaments interspersed in a tissue structure, alternatively referred to as "ciliary body" or "ciliary mass" or "ciliary process". The term "ciliary body" is used throughout the present disclosure to refer to the combination of tissues in which the muscle filaments are interspersed.

The basic principles of an AIOL applied in the present disclosure with moving optical elements are disclosed in European Patent No. 1720489, International Patent Publication No. 2007/015640, International Patent Publication No. 2006/118452 and International Patent Publication No. 2007/027091. These prior art AIOLs comprise the two optical elements and driving means driving at least one of the optical elements to execute a movement relative to the other optical element. These driving means are adapted to be coupled with the ciliary body to restore accommodation. Note that the ciliary body can drive a lens in the eye via two mechanisms. Firstly, the ciliary body can drive a lens in the eye indirectly by changing the shape of the capsular bag, which bag subsequently changes the shape of the lens, similar to functioning of the natural human lens. Secondly, the ciliary body can drive a lens in the eye directly by changing the shape of a lens via changes in inter-ciliary body distance (and, to a lesser degree, inter-sulcus distance). The present disclosure concerns such AIOLs with haptics positioned in the sulcus of the eye and constructions to use ciliary body and sulcus movements to drive the AIOL. Note that the embodiments disclosed herein apply not only to AIOLs with optics moving perpendicular to the optical axis but also to other IOLs and AIOLs and, therefore, apply to various types of AIOLs.

An AIOL must adhere to a number of strict approval and surgical requirements: for example, have sufficient accommodating power to allow full accommodation in the majority of eyes, be safe, for example, be manufactured from biocompatible materials, be preferably foldable for proper implantation, implantation preferably by injection, and the like. In addition, such lens must also be adapted to be (a) positioned in a proper, firm, and predictable position in the eye and should (b) preferably have means to adapt the basic focal power of the AIOL, for example, prior to surgery, at the end of surgery or post-surgery (after some time of wearing the lens).

Note that especially AIOLs, will provide the patient with a spectacle-free life, and that correction of, for example, far-vision post-surgery, by, for example, spectacles, is limited. Other fixed corrections of basic optical power of the eye, for example, laser treatment of the cornea, are options, but this requires additional surgery and risk. Adjustability of the IOL or AIOL itself is highly preferable. Adaptations for (a) positioning of an AIOL and (b) post-implant adjustability of optical power of an IOL, including an AIOL resulting in an AAIOL, are the subjects of the present disclosure.

SUMMARY

The present disclosure describes several exemplary embodiments of the present invention.

One aspect of the present disclosure provides an accommodating intraocular artificial lens with variable optical power, comprising: two optical elements which are adapted to mutually move in a direction perpendicular to the optical axis wherein the optical elements are shaped such that the optical elements exhibit, in combination, different optical powers at different relative positions and haptics for positioning the optical elements, wherein at least one element of the lens is adapted to be positioned in the eye in a position anterior of the capsular bag and that the haptics are adapted to extend in the sulcus of the eye.

Another aspect of the present disclosure provides an accommodating intraocular lens system, comprising: two optical elements which are adapted to mutually move in a direction perpendicular to the optical axis, and an additional optical element wherein the optical elements are shaped such that the optical elements exhibit, in combination, different optical powers at different relative positions and haptics for positioning the optical elements, wherein at least one element of the lens is adapted to be positioned in the eye in a position anterior of the capsular bag and that the haptics are adapted to extend in the sulcus of the eye.

A further aspect of the present disclosure provides a method for inserting an adjustable accommodating intraocular lens system into an eye, the adjustable accommodating intraocular lens system comprising two optical elements which are adapted to mutually move in a direction perpendicular to the optical axis, and an additional optical element wherein the optical elements are shaped such that the optical elements exhibit, in combination, different optical powers at different relative positions and haptics for positioning the optical elements, wherein at least one element of the lens is adapted to be positioned in the eye in a position anterior of the capsular bag and that the haptics are adapted to extend in the sulcus of the eye, the method comprising (a) inserting two optical elements which are adapted to mutually move in a direction perpendicular to the optical axis, the optical elements have such a shape that the optical elements exhibit, in combination, different optical powers at different relative positions into the eye; and (b) inserting an additional optical element having a constant optical power into the eye, wherein the optical power of the adjustable accommodating intraocular lens system is adjusted by adjustment of at least one of the optical elements.

Positioning of AIOL Lens in the Sulcus

IOLs are nowadays generally implanted in the capsular bag after removal of the natural lens. However, AIOL function can be severely hampered by the natural shrinkage and hardening of the capsular bag, which hardly affects a monofocal, static IOL. It is an option to position an IOL or AIOL in the sulcus of the eye, a position outside of, preferably in front of, the capsular bag. Sulcus implant was common in the past for MIOLs for which it is now occasionally used, for example, when the capsular bag has been severely damaged and can not carry an IOL.

An AIOL in the sulcus is driven mainly by the ciliary body and, to a lesser degree, the sulcus itself. Preferably, the ciliary body has to connect to or contact the posterior part of the haptics, or a second flange on the posterior optical element.

Such accommodating intraocular artificial lens with variable optical power, comprising two optical elements which are adapted to mutually move in a direction perpendicular to the optical axis wherein the optical elements have such a shape that the optical elements exhibit, in combination, different optical powers at different relative positions and haptics for positioning the optical elements can be adapted to be positioned in the eye in a position anterior, in front of, the capsular bag by adapting at least one of the elements and its haptic for such a position. In particular, the haptics, which are directly connected to the optical elements, can be adapted to extend in the sulcus of the eye. Implants of intraocular lenses with haptics positioned in the sulcus were common in the past. These were all monofocal intraocular lenses which provided only one focal spot to the eye.

Accommodating intraocular lenses implanted in the sulcus have been described in U.S. Patent Publication No. 2007/0129799, which discloses a lens with (1) optical elements which move along the optical axis, which optical elements are separate from, not connected to, (2) a circular container, which is separate from, not connected to, (3) a circular haptics ring encompassing the ciliary body. International Patent Publication No. 2005/065600 and European Patent No. 1890650 describe an AIOL which provides accommodation due to ocular pressure and lens deformation along the optical axis rather than direct driving of the construction by the ciliary muscle. The haptics of this design are implanted separately from the rest of the construction and the haptics are designed for firm positioning of the construction in the sulcus and not for movement for driving optical mechanisms. The haptics of the AIOL described in the present disclosure are arranged to extend over only at least two sections of the circumference of the optical elements and do not circumferentially enclose the complete rim of the optical elements.

The haptics may comprise positioning means (for example, flanges, extending over, at least part, of the circumference of the haptics rim) which are adapted to be at least partially enclosed by the sulcus. It should be noted that the dimensions of the flanges should be chosen such that: (a) the flanges have a width such that the flanges fit into the sulcus and that (b) the flanges have a length such that the remaining rim of the accommodating lens construction touches against the ciliary body such that the compression force and compression distance of the ciliary muscle will translate through the remaining ciliary body in a shift of the optical elements and so provide accommodation to the eye. Consequently, this provides a kind of form locking between the sulcus as a whole and those parts of the lens functioning as haptics as a whole. Alternatively, at least one the flanges can be of such shape, or an additional flange can be added to the posterior optical element, so that the ciliary body directly engages, in combination, with the fit in the sulcus for positioning. This can be accomplished with, for example, haptics which comprise annular grooves, each enclosed by two protrusions adapted to enclose at least a section of the ciliary body thus located in the groove. Also, in this particular AIOL design, the base plate of the anterior optical element can be extended to form a flange for sulcus positioning and enclosure of the ciliary body anteriorly, and the base plate of the posterior element can be extended to enclose the ciliary body posteriorly (see also FIG. 4). For all above examples, shrinkage of the bag might even be beneficial because the shrunken capsular bag will support the lens construction at the posterior part.

The haptics need to fulfil two functions, i.e., the positioning of the lens and the haptics in the sulcus and the driving of the haptics by the ciliary body in the direction perpendicular to the optical axis. In a first exemplary embodiment, the haptics extend into the sulcus and are enclosed in the sulcus between the ciliary body and the iris, wherein the driving of the haptics takes place through a rim of the haptics located at the inner side of the sulcus. In a second exemplary embodiment, the haptics extend at both sides of the ciliary body, that is, one part of the haptics extend in the sulcus and the other side in the posterior side of the ciliary body. Also in this exemplary embodiment, the driving of the haptics takes place through a face of the haptics extending at the inner side of the ciliary body. It will be clear that the positioning of the lens requires that the haptics extend over such sections of lens that a proper positioning is obtained, whereas the driving of the haptics to drive the optical elements requires at least one, but preferably at least two, opposite sections.

Also, in case the drive of the optical elements is to be provided for by the sulcus as well, it is desirable when the haptics comprise positioning hooks or claws, providing a more permanent and sturdy positioning. This leads to a kind of form locking structure, however, not between the haptics and sulcus as a whole, but between the local parts thereof. The same counts when the haptic comprises pins, an even more permanent positioning or even fixation is achieved, as the form locking comprises a kind of form locking by enclosing. Yet another exemplary embodiment resides in the application of glue, possibly in combination with other positioning means, if only for initial positioning. As an alternative, yet another exemplary embodiment provides the feature that the flanges comprise a staggered part adapted to be partially enclosed by a part of the sulcus.

It should be noted that the dimensions of the flanges should be properly chosen such that: (a) the flanges have a thickness such that the flanges fit into the sulcus and that (b) the flanges protrude equally from two sides of the rim which, in turn, compresses the zonulae and touches against the ciliary body such that the compression force and compression distance of the ciliary muscle will translate through the remaining ciliary body in a shift of the optical elements.

However, other means of positioning or 'suturing' are not excluded. Clearly, flange diameters should be chosen carefully to maximize ciliary body function on the AIOL in case additional flanges are added to enclose the ciliary body in a posterior and anterior plane.

Adjustability of Accommodating Intraocular Lens

All intraocular lenses, or lens systems, must have a basic optical power to correct the total refraction of the eye, resulting in an emmetropic eye, i.e., an eye which provides a sharp image at a distance. Standard fixed optical power intraocular lenses provide only this optical power, accommodating intraocular lenses can add variable power on top of this base power. However, in practice, emmetropia of eye is hardly ever reached despite modern refraction measuring equipment. The achieved refraction generally deviates by 0.5 to 1D from the desired refraction. Means to adjust any intraocular lens, including AIOLs, after implant are desirable. Note that for standard monofocal intraocular lenses the patient will have to wear spectacles anyway (generally, progressive spectacles) to which a minor correction for emmetropia can be easily added by the optician. However, true AIOLs promise a spectacle-free life, and such correction on spectacles is an option not preferred. In any case, pre-implant (prior to surgery), post-implant (at the end of surgery) or post-surgery (at any time after surgery) adjustability can benefit any IOL, including standard monofocal MIOLs.

In the AIOL design as disclosed, adjustability can be achieved by, for example, changing the size (shortening or lengthening) of at least one haptic which will shift the optical elements to a new resting position, as described in Dutch Patent Application No. 1028496 (FIG. 6) by application of a notches and grooves mechanical calibration system.

The optical power of an IOL or AIOL can be adapted or adjusted by, for example, the addition of at least one additional optical element, being a second optical element (in the case of, for example, monofocal, MIOL, or multifocal IOL) or being a third optical element (in the case of the AIOL designs as disclosed in this document which consist of two optical elements), which additional optical element can be integrated with the IOL or MIOL or AIOL, or the additional optical element can be separate from the IOL or MIOL or AIOL. The additional optical element has constant optical power, can be non-adjustable or adjustable (which is, when adjustable, only occasionally changed), can be added during surgery or added to the system after implantation (or, alternatively, adjustability by removal of an additional optical element). Addition of an additional optical element results in an adjustable AIOL system ("AAIOL system"), which additional optical element can be adapted to be positioned in the anterior or, alternatively, in the posterior chamber of the eye, in contact with or separate from the IOL or MIOL or AIOL.

With regard to the AIOL of the present disclosure, an additional optical element (in this case, a third optical element) can be an integral component of the adjustable AIOL system, i.e., physically connected to any component of the AIOL, for example, by a mechanical or chemical connection, which connection can be a rigid connection or an elastic connection. However, the third optical element can also be separate from the AIOL, for example, the third optical element be positioned in a different part of the eye. For example, an AAIOL system with the AIOL positioned in the sulcus and the additional third element positioned in the capsular bag. Firstly, the third element can be a lens fitted into an enclosure of the AIOL specifically adapted to enclose or be attached to the third optical element. Secondly, such lens can be positioned in the eye completely separate from the accommodating intraocular lens. For example, an AIOL positioned in the sulcus, as described hereinabove in combination with a lens in the capsular bag. Other combinations and positions are possible. Such lens can be a simple spherical lens of low optical value, for example, 0.5D, and additionally contain surfaces to correct for other aberrations of the eye, for example, astigmatism. Also, such third element lens can be of fixed optical power or of an adjustable optical power. Intraocular lenses adjustable for optical power have recently become available, such as those disclosed in International Patent Publication No. 03/058287.

Also, the third optical element can have at least one optical surface which forms a lens of variable optical power in combination with at least one additional optical surface on at least one of the optical elements of the AIOL of which the optical power varies with different positions of the additional surfaces relatively to each other. The power of the lens varies with lateral shift of the additional elements or, alternatively, a rotation of the additional element.

Various exemplary embodiments can be designed with a fixed-dioptric power lens (or, alternatively, a fixed-diopter adjustable power lens; the power is fixed in normal life, but only occasionally adjusted by an eye surgeon to ensure emmetropia of the un-accommodated eye) implanted in the capsular bag and a spatially separated accommodating optical element with flanges positioned in the sulcus of the eye. For example, in such a configuration the fixed-power lens, i.e., a standard monofocal IOL which replaces the natural lens, corrects for emmetropia, whereas the accommodative element, having a zero base refraction, delivers only the variable focusing power by the mutually shift in a direction perpendicular to the optical axis of the optical elements. Note that in all examples in the present disclosure, the surfaces of the optical elements which mutually shift in a direction perpendicular to the optical axis can be designed to either add or subtract optical power when moved in a certain direction. For the eye, however, an increase in diameter of the sulcus and ciliary body means a reduction in optical power of the natural lens. It is logical that an accommodating IOL adheres to those same principles. Also, note that for all examples in the present disclosure, the fixed optical power can be distributed over a fixed lens and the accommodative element. For example, the fixed element can have 20D to which 0-5D is added by the accommodative element or, for example, the fixed element can have 18D to which 2-7D is added by the accommodative element.

Several important advantages of uncoupled optics for refractive power and accommodation can be outlined: (i) the implantation of each optic can be accomplished by a standard IOL injector through a small incision reducing trauma to the patient eye; (ii) the constant power lens in the capsular bag limits shrinkage of the capsular bag and closes access to the anterior part of the posterior section of the capsular bag for floating cells which may cause PCO (posterior capsular opacification); and, (iii) the accommodative element positioned in the sulcus of the eye is not affected by the capsular bag shrinkage.

Accommodating IOL systems, with a component of shifting optical elements, can be comprised of a fixed lens, for example, a standard plate haptic or C-loop IOL, implanted in the capsular bag in its standard position in combination with a separate accommodating optical element with flanges positioned in the sulcus of the eye.

Other exemplary embodiments have an accommotative element for a presbyopic/phakic eye, i.e., an eye which still contains a transparent, non-cataracterous, but inelastic, non-accommodating, natural lens. Such separate accommodative element can restore accommodation and must be implanted outside the capsular bag in which the natural lens remains. Such implant can be positioned, for example, in the sulcus or in any other position in the eye where accommodative movement can be obtained to shift at least one optical element.

It is also possible to adapt the AAIOL with such a construction so that a shift can be provided of at least one optical element able to shift the basic refractive element along the optical axis. Such shift will also result in adjustment of the power of the AAIOL within the context of the optical system of the eye.

The adjustable accommodating optical lens system can be a complete unit inserted in one exemplary procedure by, for example, injection. However, a method for inserting an AAIOL system into an eye comprises the following steps: (a) inserting two optical elements which are adapted to mutually move in a direction perpendicular to the optical axis, the optical elements have such a shape that the optical elements exhibit, in combination, different optical powers at different relative positions into the eye and, (2) inserting a third, adjustable, optical element having a constant optical power into the eye. Adjustment can take place prior to surgery, during surgery (for example, just before the end of surgery, after the AAIOL is implanted in the eye) or after surgery (for example, several month after surgery when the eye is supposed to have healed and be stabilized, or, alternatively, years after surgery when the optical requirements of the eye can have changed due to aging). The optical power of the adjustable accommodating intraocular lens system is adjusted after implantation in the eye. The adjustment of the optical power can take place by amendment of the relative position of the optical element to the accommodating intraocular lens or the adjustment of the optical power takes can take place by insertion of the additional optical element to the accommodating intraocular lens.

BRIEF DESCRIPTION OF THE DRAWINGS

Various aspects of the present disclosure are described hereinbelow with reference to the accompanying figures.

DETAILED DESCRIPTION

Figure 1:
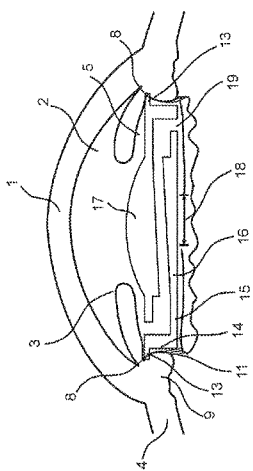
FIG. 1 is a schematic view of the natural eye.

FIG. 1 shows the basic schematics of the anterior part of the human eye. Note that in this particular example the eye is likely un-accommodated because the zonules are tense and the lens slightly flattened. Behind the cornea of the eye 1 is the anterior chamber 2 the iris 3 and the sclera 4. The posterior chamber 5 is the space between the iris and the capsular bag 6 which contains the natural lens 7. The sulcus 8 is positioned between the iris and the ciliary body 9, wherein its width is indicated by the arrow 10 and is connected to several groups of zonules 11 and also includes the ciliary muscle. The arrow 12 indicates the distance over which the zonules can be collapsed.

Figure 2:
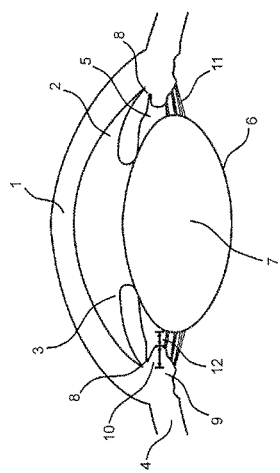
FIG. 2 is a schematic view of the eye with an AIOL with flanges in the un-accommodated state according to one exemplary embodiment of the present invention.
Figure 3:
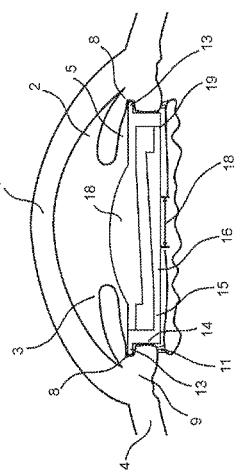
FIG. 3 is a schematic view of the eye with an AIOL with flanges in the accommodated state according to one exemplary embodiment of the present invention.

FIGS. 2 and 3 show schematic views of the anterior part of the eye with an AIOL with flanges 13 positioned in the sulcus. The rim of the haptic of the accommodating intraocular lens 14 is in contact with the ciliary body. The haptic is connected via a connector 15 to either the posterior element 16 or the anterior optical element 17. Note that complex surfaces which form a lens of variable optical power are schematically represented by two slanting surfaces on the inner side of each optical element. The capsularrhexis 18 is the opening through which the natural lens is removed. The elastic connection spring which allows the optical element to shift has an opening 19 which is open when the lens is in an un-accommodated state of low dioptric power as shown in FIG. 2 and closed when the lens is in an accommodated state of high dioptric power as shown in FIG. 3. In both figures, the rim of the haptics implanted anterior of the capsular bag has flanges 13 supporting the lens construction positioned in the sulcus. The length of the flanges is designed to position the rim of the optical elements of the AIOL construction at the ciliary body to allow the ciliary muscle to shift the optical elements.

Figure 4:
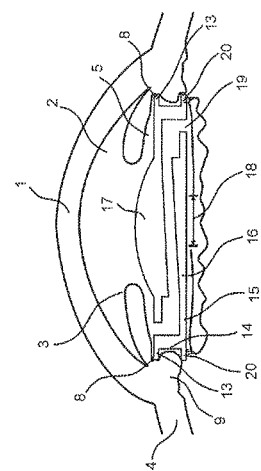
FIG. 4 is a schematic view of the embodiment of FIG. 2 with an additional posterior flange forming a groove in combination with the anterior flange.

FIG. 4 shows a schematic of the anterior part of the eye with an AIOL with additional posterior flanges 20, additional to the anterior flanges illustrate in FIGS. 2 and 3 to support positioning and embracing the ciliary body.

Figure 5:
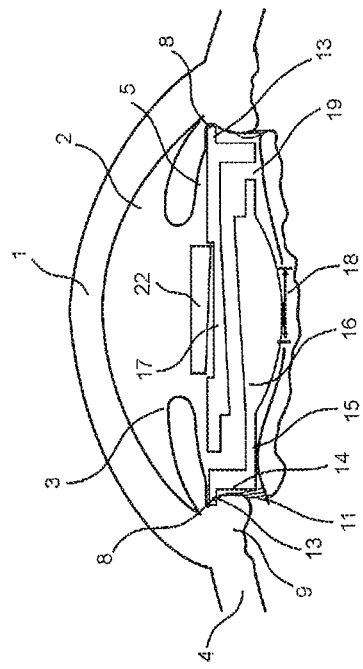
FIG. 5 is a schematic view of one exemplary embodiment of the eye with an AIOL (without basic refractive optics, only with accommodating optics) in combination with a separate fixed optical power or, alternatively, a fixed adjustable optical power lens, in this example, in the capsular bag.

FIG. 5 shows a schematic view of the anterior part of the eye with an AIOL as in earlier figures but without a basic refractive optics in combination with a basic refractive lens 21 implanted separately in the capsular bag. This lens can be either of fixed optical power or, alternatively, an adjustable lens. The relaxed state, or the un-accommodated, is shown; the accommodated state follows FIG. 3.

Figure 6:
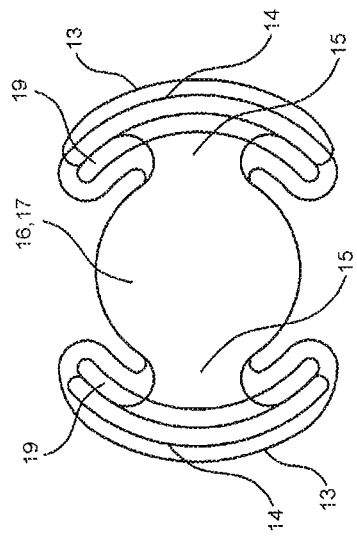
FIG. 6 is a schematic view of a second exemplary embodiment of the eye with an AIOL with flanges and a posterior basic refractive optics in combination with a third optical element, in this example, an element with such a shape that movement of this element optical results in a variable lens in combination with an optical surface on any of the optical elements of the accommodative lens.

FIG. 6 shows a schematic view of the eye with an AIOL with flanges and a posterior optical element which also carries basic refractive optics in combination with a third optical element 22, in this exemplary embodiment, an element with such a shape that movement of this element (for example, shift or rotation) results in a variable lens, in combination with an optical surface on any of the other optical elements of the accommodative lens.

Figure 7:
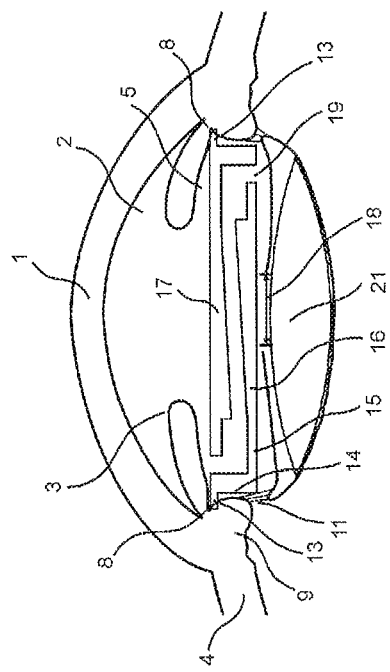
FIG. 7 is a schematic view of a third exemplary embodiment of the eye with an AIOL with flanges and a posterior basic refractive optics in combination with a third optical element, in this example, a fixed optical power or, alternatively, a fixed adjustable optical power lens, wherein this third optical element is a plano-convex lens fitted into an enclosure.

FIG. 7 shows a schematic view of the eye with an AIOL with flanges and a posterior basic refractive optics in combination with a third optical element 23, in this exemplary embodiment, a lens of fixed optical power which can be adjustable. In this exemplary embodiment, a plano-convex lens is fitted into an enclosure with holding means 24.

Figure 8:
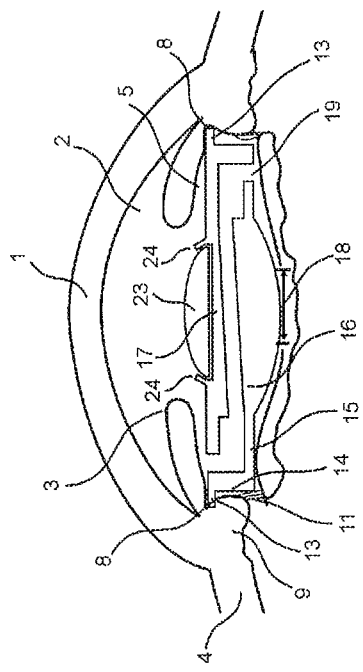
FIG. 8 is a schematic view of the AIOL with flanges for positioning in the sulcus, seen from above, according to one exemplary embodiment.

FIG. 8 shows a schematic outline of the AIOL with flanges for positioning in the sulcus, seen from above. Note that all accommodating lenses described hereinabove can also have the option to correct for aberrations of the overall optics of the eye, for example, astigmatism.

A number of exemplary embodiments for positioning as well as adjustability will be outlined hereinbelow. However, it will be clear to one of ordinary skill in the art that other embodiments for positioning in the sulcus of the eye of an AIOL as well as adjustability post-implant of any IOL, including any AIOL, within the scope of the appended claims may be devised.

Sulcus Positioning

One exemplary embodiment (shown in FIGS. 2 and 3) for positioning of the AIOL described in the sulcus has flanges 13 which extend from the base plate of the anterior element of the AIOL. The flanges have the appropriate width to ensure proper fit in the sulcus and have the appropriate length to ensure that the ciliary body is in contact with the rim 14 of the main body of the AIOL. At accommodation (FIG. 3), the ciliary body and, to a degree, the sulcus, will move the optical elements of the AIOL to a position of higher optical diopter power compared to the relaxed state (FIG. 2).

In a second exemplary embodiment (FIG. 4), similar flanges extend from both the anterior element as well as the posterior element, with flanges 20. In this exemplary embodiment, the ciliary body is enclosed by the four flanges and a transfer of force and movement of both ciliary body and the sulcus is ensured.

Both exemplary embodiments have already shown to be simply manufactured by a straightforward addition to the milling program to extend the base plate to form the flanges. Clearly, such lenses can comprise other constructions to extend the flanges, for example, extension of base plates by metal inserts, additional components, and so forth, but such additional components appear to be complex solutions to the same effect.

Adjustability

Firstly, one exemplary embodiment comprises the addition of an adjustable (for example, a light adjustable MIOL lens to the accommodative lens, resulting in an AAIOL system (see, for example, International Patent Publication No. WO 03/058287). FIG. 5 shows the addition of such an adjustable MIOL in the capsular bag. Clearly, the refractive power of the AIOL must be reduced in case of such addition and the power of the refractive unit.

Secondly, not illustrated, such an adjustable lens can be directly attached to the posterior or anterior element of the AIOL by gluing or by a number of mechanical means. Post-surgery adjustment of the adjustable lens provides an AAIOL which ensures emmetropia of the eye. Note that such adjustments are reversible and that such adjustments can be repeated several times.

The AIOL of the present disclosure changes the optical power of a lens formed by two optical elements which move perpendicular to the optical axis. Such a concept can be applied to add adjustability to the AIOL as well. A third optical element 22 (FIG. 6) is added to the AIOL, of which at least one surface forms a variable lens in combination with an additional surface on any of the surfaces of the AIOL. The lens varies in optical power by either shift of the third element or, alternatively, by rotation over an axis, with the third element preferably connected to the AIOL by an elastic connection. Alternatively, such third element 23 can be added to the AIOL by holding means (in an enclosure) 24. Such (occasional, adjusting) shift or rotation of the third element is most likely achieved by interference by an eye surgeon by moving the element in the eye by, for example, a surgical needle or forceps, through a small incision. However, electro-mechanical or magnetic or optical (by, for example, a surgical laser) options for such movement are possible with adaptations to the AIOL system.

Most simply, at least one holding means (in this example, partial enclosure) 24 (FIG. 7) formed, in this example, by a rim or, alternatively, by at least two clamps can be designed to either partially enclose a low power MIOL or partially enclose an adjustable low power MIOL (or a third element with a complex optical surface which works in combination with an additional surface on the AIOL, as set forth hereinabove). Such MIOL or third element can be added before surgery (at the manufacturing stage), during surgery, or post-surgery (at any time). Such MIOL can be of a low positive or low negative power (for example, in the range of −2D to +2D), depending on requirements. Such MIOL can be thin (~100-200 um thick) ensuring simple surgery through a small incision and hardly add to the thickness of the anterior optical element of the AAIOL (as shown in FIG. 7).

All patents, patent applications, publications and other documents referred to herein are incorporated by reference in their entirety.

The invention claimed is:

1. An accommodating intraocular artificial lens (IOL) with variable optical power and having an optical axis, the lens comprising:

a main body comprising an anterior baseplate, a posterior baseplate, and two opposite arched rims;

the anterior baseplate comprising a central anterior optical element and at least two opposite haptics positioned in a plane perpendicular to the optical axis of the eye, wherein the anterior optical element has a posterior slanted optical surface, wherein at least one haptic of the anterior baseplate has an arcuate spring-like structure adapted to be compressed in a direction perpendicular to the optical axis;

the posterior baseplate comprising a central posterior optical element and at least two opposite haptics positioned in a plane perpendicular to the optical axis of the eye, wherein the posterior optical element has an anterior slanted optical surface, wherein at least one haptic of the posterior baseplate has an arcuate spring-like structure adapted to be compressed in a direction perpendicular to the optical axis;

wherein the haptics of the anterior baseplate are circumferentially connected to the haptics of the posterior baseplate by said two opposite arched rims, wherein each of the arched rims extends in a direction parallel to the optical axis, and wherein each of the arched rims comprises a ciliary body-engaging surface adapted to engage the ciliary body and adapted to transfer force and movement of the ciliary body to the spring-like structures of the haptics of the anterior and posterior baseplates, wherein each of the two optical elements have a shape that they exhibit, in combination, different optical powers at different positions of one optical element relative to the other optical element, wherein the spring-like structures of the haptics of the anterior and posterior baseplates mutually shift the optical elements in opposite directions relative to each other along a direction perpendicular to the optical axis, wherein each of the spring-like structures of the haptics of the anterior and posterior baseplates comprises an arcuate opening which is open when the intraocular lens is in an un-accommodated state, and which is closed when the intraocular lens is in an accommodated state, wherein at least the anterior optical element of the lens is adapted to be positioned anterior of a capsular bag in an eye, wherein at least one haptic of the anterior baseplate comprises a sulcus-engaging positioning flange adapted to extend in the sulcus of the eye and to be partially enclosed by the sulcus, and wherein at least one haptic of the posterior baseplate comprises a sulcus-engaging positioning flange adapted to extend in the sulcus of the eye and to be partially enclosed by the sulcus.

2. The accommodating intraocular lens of claim 1, wherein the haptics are adapted to engage the ciliary body.

3. The accommodating intraocular lens of claim 2, wherein the haptics comprise at least two annular grooves each enclosed by two flanges adapted to enclose at least a section of the ciliary body.

4. The accommodating intraocular lens as claimed in claim 2, wherein the rim is adapted to touch the ciliary body such that a compression force and compression distance of the ciliary muscle will translate through the remaining ciliary body in a shift of the optical elements.

5. The accommodating intraocular lens of claim 1, wherein the optical elements are adapted to be combined with at least one additional optical element having a constant optical power and being adapted to be located in the optical axis of the eye.

6. The accommodating intraocular lens system, comprising the accommodating intraocular artificial lens of claim 1 and an additional optical element.

7. The accommodating intraocular lens system of claim 6, wherein the additional optical element is located separate from the accommodating intraocular lens.

8. The accommodating intraocular lens system of claim 7, wherein the additional optical element is adapted to be located behind the iris.

9. The accommodating intraocular lens system of claim 6, wherein the additional optical element is adapted to be located in the anterior eye chamber.

10. The accommodating intraocular lens system of claim 6, wherein the additional optical element is mechanically connected to the accommodating intraocular lens.

11. The accommodating intraocular lens system of claim 10, wherein the accommodating intraocular lens includes holding means adapted to hold the additional optical element.

12. The accommodating intraocular lens system of claim 11, wherein the holding means are adapted to receive the additional optical element after the accommodating intraocular lens has been implanted in the eye.

13. The accommodating intraocular lens system of claim 6, wherein the additional optical element is adapted to have its optical power adjusted after it has been inserted into the eye.

14. The accommodating intraocular lens system of claim 13, wherein the additional optical element has a first shape and that one of the optical elements of the accommodating optical lens has a second shape, wherein the first and second shape have such properties that the additional optical element and the accommodating optical element exhibit, in combination, different optical powers at different relative positions.

15. The accommodating intraocular lens as claimed in claim 1, wherein at least one of the optical elements comprises a surface providing a constant optical power.

* * * * *